(12) United States Patent
Norton (10) Patent No.: US 6,372,506 B1
(45) Date of Patent: Apr. 16, 2002

(54) APPARATUS AND METHOD FOR VERIFYING DROP DELAY IN A FLOW CYTOMETER

(75) Inventor: Pierce Owen Norton, Morgan Hill, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/346,692

(22) Filed: Jul. 2, 1999

(51) Int. Cl.⁷ .............................................. G01N 33/48
(52) U.S. Cl. ............................ 436/63; 422/73; 209/3.2; 209/4; 209/127.4; 209/552; 209/576; 209/906
(58) Field of Search .................... 436/63, 164; 422/73, 422/82.05; 250/461.2; 209/3.1, 3.2, 3.3, 4, 552, 571, 576–579, 127.4, 906

(56) References Cited

U.S. PATENT DOCUMENTS

| | | | |
|---|---|---|---|
| 3,960,449 A | | 6/1976 | Carleton et al. ............. 356/340 |
| 4,318,483 A | * | 3/1982 | Lombardo et al. ........... 209/3.1 |
| 4,347,935 A | | 9/1982 | Merrill ........................ 209/3.2 |
| 4,487,320 A | * | 12/1984 | Auer ........................... 209/3.1 |
| 4,667,830 A | | 5/1987 | Nozaki, Jr. et al. .......... 209/3.1 |
| 4,981,580 A | * | 1/1991 | Auer ........................... 209/3.1 |
| 5,464,581 A | | 11/1995 | van den Engh .......... 422/82.01 |
| 5,483,469 A | | 1/1996 | Van den Engh et al. ...... 702/21 |
| 5,602,039 A | | 2/1997 | Van den Engh ............ 436/164 |
| 5,643,796 A | | 7/1997 | Van den Engh et al. ...... 436/50 |
| 5,700,692 A | | 12/1997 | Sweet ......................... 436/50 |
| 5,916,449 A | * | 6/1999 | Ellwart et al. ............... 210/745 |
| 5,998,212 A | * | 12/1999 | Corio et al. ................... 436/63 |
| 6,079,836 A | * | 6/2000 | Burr et al. ..................... 356/70 |
| 6,133,044 A | * | 10/2000 | Van den Engh ............ 436/177 |
| 6,248,590 B1 | * | 6/2001 | Malachowski ............... 436/63 |

* cited by examiner

Primary Examiner—Maureen M. Wallenhorst
(74) Attorney, Agent, or Firm—Alan W. Fiedler (57) ABSTRACT

An apparatus and method for verifying the drop delay in a flow cytometer, which is indicative of the time that elapses from a moment at which a particle of interest is detected at an interrogation point in the flow of cytometer to the moment at which a sorting condition, such as a charging potential, is applied in response to the detection to a droplet forming at a droplet forming location in the flow cytometer. The apparatus and method analyzes the content of the droplets formed by the flow cytometer, and based on the analysis, provides an indication as to whether the drop delay time at which the flow cytometer is operating is correct. Specifically, the charging potential should be applied to the droplet containing the detected particle of interest. The content of the droplets can be analyzed at the droplet formation point, or at a location downstream of the droplet formation point, to detect the presence or absence of a particle of interest that was detected at the interrogation point in the flow cytometer. The drop delay time at which the droplets being formed by the flow cytometer are charged can then be set based on the results of the analysis of the content of the droplets, to ensure that droplets containing particles of interest are charged and thus sorted by the flow cytometer, while droplets not including particles of interest remain uncharged and are not sorted.

22 Claims, 7 Drawing Sheets

APPARATUS AND METHOD FOR VERIFYING DROP DELAY IN A FLOW CYTOMETER

BACKGROUND OF THE INVENTION

The present invention relates to an apparatus and method for verifying the drop delay in a flow cytometer. More particularly, the present invention relates to an apparatus and method which detects the presence or absence of particles of interest in fluid droplets formed by a flow cytometer to determine whether the time at which the fluid droplets are being charged is correct, so that the droplets can be sorted electrostatically with precision.

Flow cytometers known in the art are used for analyzing and sorting particles in a fluid sample, such as cells of a blood sample or particles of interest in any other type of biological or chemical sample. A flow cytometer typically includes a sample reservoir for receiving a fluid sample, such as a blood sample, and a sheath reservoir containing a sheath fluid. The flow cytometer transports the particles (hereinafter called "cells") in the fluid sample as a cell stream to a flow cell, while also directing the sheath fluid to the flow cell.

Within the flow cell, a liquid sheath is formed around the cell stream to impart a substantially uniform velocity on the cell stream. The flow cell hydrodynamically focuses the cells within the stream to pass through the center of a laser beam. The point at which the cells intersect the laser beam, commonly known as the interrogation point, can be inside or outside the flow cell. As a cell moves through the interrogation point, it causes the laser light to scatter. The laser light also excites components in the cell stream that have fluorescent properties, such as fluorescent markers that have been added to the fluid sample and adhered to certain cells of interest, or fluorescent beads mixed into the stream.

The flow cytometer further includes an appropriate detection system consisting of photomultiplier tubes, photodiodes or other light detecting devices, which are focused at the intersection point. The flow cytometer analyzes the detected light to measure physical and fluorescent properties of the cell. The flow cytometer can further sort the cells based on these measured properties.

To sort cells by an electrostatic method, the desired cell must be contained within an electrically charged droplet. To produce droplets, the flow cell is rapidly vibrated by an acoustic device, such as a piezoelectric element. The droplets form after the cell stream exits the flow cell and at a distance downstream from the interrogation point. Hence, a time delay exists from when the cell is at the interrogation point until the cell reaches the actual break-off point of the droplet. The magnitude of the time delay is a function of the manner in which the flow cell is vibrated to produce the droplets, and generally can be manually adjusted, if necessary.

To charge the droplet, the flow cell includes a charging element whose electrical potential can be rapidly changed. Due to the time delay which occurs while the cell travels from the interrogation point to the droplet break-off point, the flow cytometer must invoke a delay period between when the cell is detected to when the electrical potential is applied to the charging element. This charging delay is commonly referred to as the "drop delay", and should coincide with the travel time delay for the cell between the interrogation point and the droplet break-off point to insure that the cell of interest is in the droplet being charged.

At the instant the desired cell is in the droplet just breaking away from the cell stream, the charging element is brought up to the appropriate potential, thereby causing the droplet to isolate the charge once it is broken off from the stream. The electrostatic potential from the charging circuit cycles between different potentials to appropriately charge each droplet as it is broken off from the cell stream.

Because the cell stream exits the flow cell in a substantially downward vertical direction, the droplets also propagate in that direction after they are formed. To sort the charged droplet containing the desired cell, the flow cytometer includes two or more deflection plates held at a constant electrical potential difference. The deflection plates form an electrostatic field which deflects the trajectory of charged droplets from that of uncharged droplets as they pass through the electrostatic field. Positively charged droplets are attracted by the negative plate and repelled by the positive plate, while negatively charged droplets are attracted to the positive plate and repelled by the negative plate. The lengths of the deflection plates are small enough so that the droplets which are traveling at high velocity clear the electrostatic field before striking the plates. Accordingly, the droplets and the cells contained therein can be collected in appropriate collection vessels downstream of the plates.

Known flow cytometers similar to the type described above are described, for example, in U.S. Pat. Nos. 3,960,449, 4,347,935, 4,667,830, 5,464,581, 5,483,469, 5,602,039, 5,643,796 and 5,700,692, the entire contents of each patent being incorporated by reference herein. Other types of known flow cytometer, are the FACSVantage™, FACSort™, FACSCount™, FACScan™ and FACSCalibur™ systems, each manufactured by Becton Dickinson and Company, the assignee of the present invention.

As can be appreciated from the foreign description, in order for a flow cytometer to correctly sort cells of interest, the drop delay must be precisely measured to ensure that a cell of interest which was detected at the interrogation point is actually present in the droplet being charged. If the drop delay is not accurately determined, it is likely that the charge will be applied to a droplet formed earlier or later than the droplet containing the cell of interest. In this event, the droplet containing the cell of interest will not be charged, and therefore will not be sorted as desired. Rather, an incorrectly charged droplet will be sorted, thus reducing the overall sorted cell count, or adding an unwanted cell to the cell count if that droplet contains an unwanted cell.

Several known methods exist for calculating the drop delay with reasonable accuracy. In one known method, the distance between the interrogation point and the droplet formation (break-off) point is measured using, for example, a graduated optical measuring tool. The measuring tool is then repositioned so that the graduation originally positioned at the interrogation point is moved to the droplet break-off point, and the graduation originally positioned at the droplet break-off point is positioned in the droplet stream. The number of droplets appearing between the graduation positioned at the droplet break-off point and the graduation in the droplet stream is then counted, and the drop delay is expressed as the number of counted drops.

For example, if the number of counted drops appearing between the graduations is equal to five, this indicates that five drop periods elapse form the time a cell is at the interrogation point until it reaches the droplet break-off point. Accordingly, the charge timing of the flow cytometer is set so that charging intended to be applied to a droplet containing a cell of interest is delayed by five drop periods from the time when the cell of interest is detected at the interrogation point.

Although this method generally enables the flow cytometer to charge the correct droplets, and therefore sort the cells of interest with reasonable accuracy, the method provides no means to verify the accuracy of the charge timing while cell sorting is being performed. Rather, the results of the sort must be examined after all or at least a portion of the sorting process has been completed. If, upon examination of the results, it is determined that the charge timing was incorrect, the process must be repeated until the correct charge timing is determined. Furthermore, because the method requires multiple steps, such as aligning the graduations on the optical instrument with the appropriate points at different positions along the droplet stream, the process can be somewhat time consuming even if the charge timing is correctly set on the initial attempt.

Instead of attempting to estimate the drop delay as in the method described above, another known method exists in which a number of sort results are obtained for a calibration sample sorted at different droplet charge timing settings, and the sort results are empirically checked. That is, before attempting to sort an actual cell sample, the sample reservoir is filled with sample particles, commonly known as "beads", which have physical and fluorescent characteristics similar to those of the cells of interest in the actual sample. The flow cytometer is run for a time period during which a predetermined number of beads (for example, 40 beads) should be sorted, with the drop delay for charging being set at a first estimated setting. As the cells are being sorted, they are collected on an area of a collection medium, such as a glass slide suitable for viewing under a microscope.

The sorting is then performed again for the same amount of time with the drop delay for charging being set at a slightly different value, and the sorted cells are collected on a different area of the collection medium. An additional number of sorts are performed, with the drop delay being set differently for each sort, and with the results of each sort being collected at a different region on the collection medium. After the desired number of sorts have been performed, each sorted sample on the collection medium is viewed under a microscope, and the number of beads actually sorted for each sorted operation is counted. The drop delay yielding the highest number of sorted cells is then determined to be the most appropriate drop delay at which the actual cell samples should be sorted.

Although this method enables the drop delay to be set with reasonable accuracy, the method requires that multiple sorts be performed on the sample beads, and thus is fairly time consuming. The sample collection medium must be removed from the flow cytometer and examined under a microscope to analyze the samples, thus making the process more complicated and subject to error. Also, because the number of cells in each of the collected samples must be counted manually, the time required to complete the analysis is further increased, and additional opportunity for error is introduced. In addition, the method provides no means to verify the accuracy of the charge timing while the sorting operation is being performed Accordingly, a need exist for an efficient and reliable apparatus and method for detecting the drop delay in a flow cytometer, so that the drop delay can be accurately set and maintained to insure reliable cell sorting.

SUMMARY OF THE INVENTION

An object of the present invention is to provide an accurate and reliable apparatus and method for verifying the accuracy of the drop delay in a flow cytometer, so that flow cytometer can accurately charge droplets containing particles of interest to insure that the particles of interest are sorted with high reliability.

Another object of the invention is to provide an apparatus and method for setting the drop delay at which droplets are charged while the flow cytometer is performing the process of sampling and sorting particles of interest.

A further object of the invention is to provide an apparatus and method which analyzes the contents of droplets formed in a flow cytometer to determine whether the droplets are being charged at the appropriate drop delay so that droplets containing particles of interest are sorted in the appropriate manner.

These and other object of the present invention are substantially achieved by providing an apparatus and method for verifying the drop delay in a flow cytometer. The drop delay is defined as the period that elapses from the moment at which a particle of interest is detected at an interrogation point in the flow cytometer to the moment at which a charging device applies a charging potential to the droplet forming at the droplet break-off point. Preferably, the drop delay should coincide with the amount of time that elapses for the particle of interest to travel from the interrogation point to a location that substantially coincides with the droplet break-off point. The apparatus and method analyzes the content of the droplets formed by the flow cytometer, and based on the analysis, determines the drop delay at which the flow cytometer should be operating. The content of the droplets can be analyzed to detect for the presence or absence of a particle of interest that was detected at the interrogation point in the flow cytometer. The drop delay at which the droplets being formed by the flow cytometer are charged can then be set based on the results of the analysis of the contents of the droplets, to ensure that droplets containing particles of interest are charged and thus sorted by the flow cytometer, while droplets not including particles of interest remain uncharged and are not sorted.

The apparatus and method preferably employs non-contact sensors, such as light detectors or the like, for analyzing the content of the droplets. The content of the droplets can be analyzed at the droplet break-off point at which the droplets are initially formed, or at any location in the uncharged or charged droplet streams.

BRIEF DESCRIPTION OF THE DRAWINGS

The various objects, advantages and novel features of the present invention will be more readily appreciated from the following detailed description when read in conjunction with the accompanying drawings, in which.

DETAILED DESCRIPTION OF THE PREFERRED EMBODIMENTS

A flow cytometer 100 employing an embodiment of the present invention is illustrated in FIGS. 1–5. As discussed in the background section above, the flow cytometer 100 includes a nozzle 102 having a flow cell 104 therein. The flow cytometer further includes a sample reservoir 106 for receiving a fluid sample, such as a blood sample, and a sheath reservoir 108 containing a sheath fluid. The flow cytometer transports the cells in the fluid sample in the cell stream to the flow cell 104, while also directing the sheath fluid to the flow cell 104.

Within the flow cell 104, the sheath fluid surrounds the cell stream, and the combined sheath fluid and cell stream exits the flow cell 104 via an opening 110 as a sample stream. The opening 110 can have a diameter of, for example, 50 μm, 70 μm, 100 μm, or any other suitable diameter. As illustrated, due to characteristics of the sheath fluid, such as surface tension and the like, the sample stream remains intact until breaking off into droplets at the droplet break-off point 112, which is at a certain distance from opening 110. The distance from opening 110 at which the droplet breakoff point 112 occurs, and the frequency or rate at which the droplets are formed, are governed by the fluid pressure, as well as the amplitude and frequency of oscillation of oscillating device 114 which can be, for example, a piezoelectric element.

Figure 2:
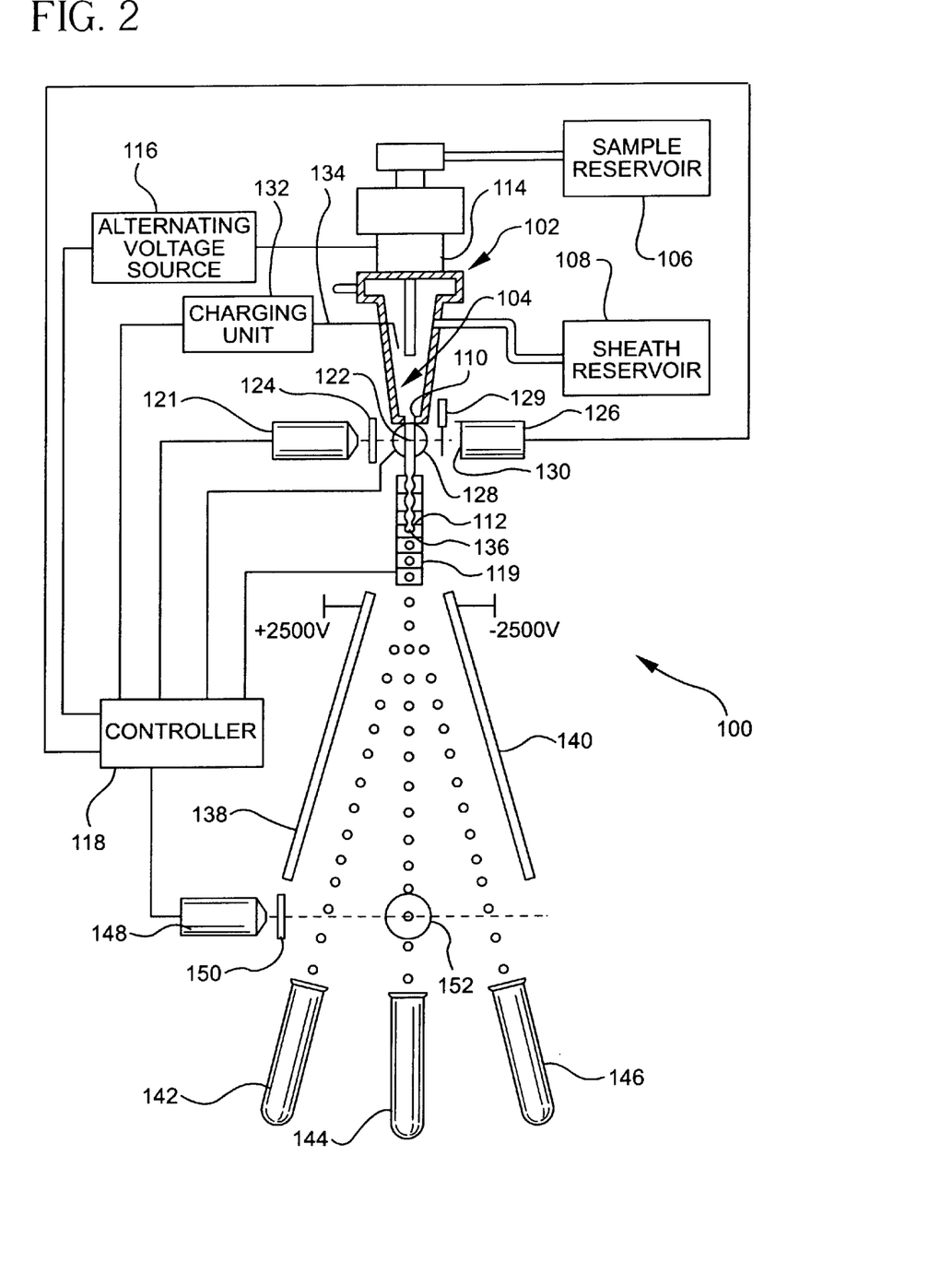
FIG. 2 is a schematic illustration of a front view of a portion of the flow cytometer shown in FIG. 1.
Figure 3:
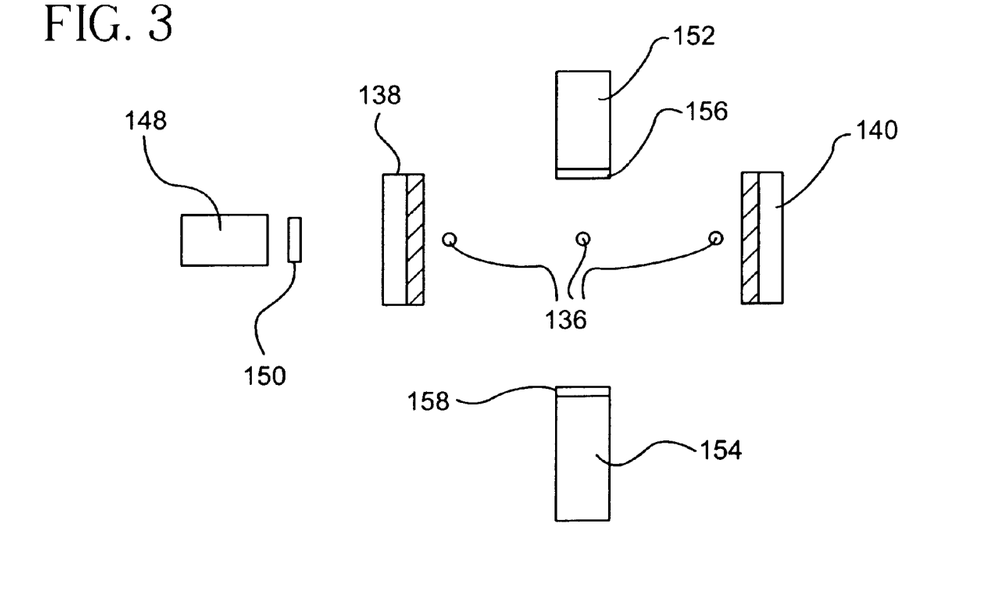
FIG. 3 is a view of a portion of the flow cytometer shown in FIG. 1 taken along lines 3—3.
Figure 4:
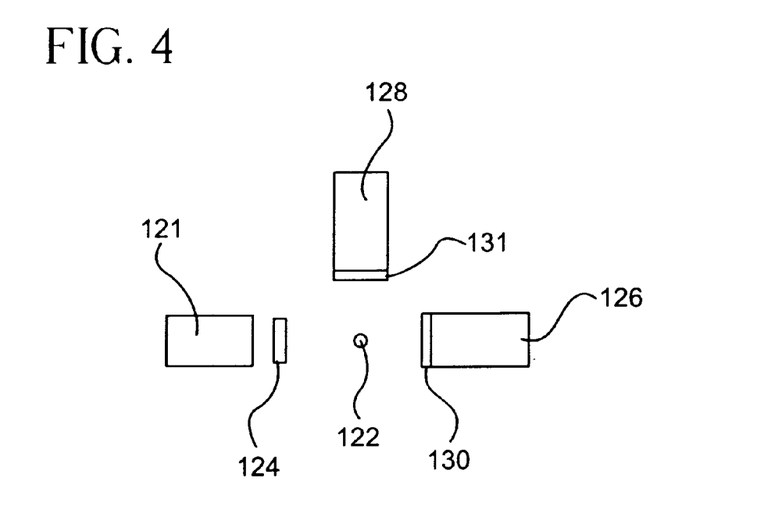
FIG. 4 is a schematic illustration of a portion of the flow cytometer shown in FIG. 1 taken along lines 4—4.
Figure 5:
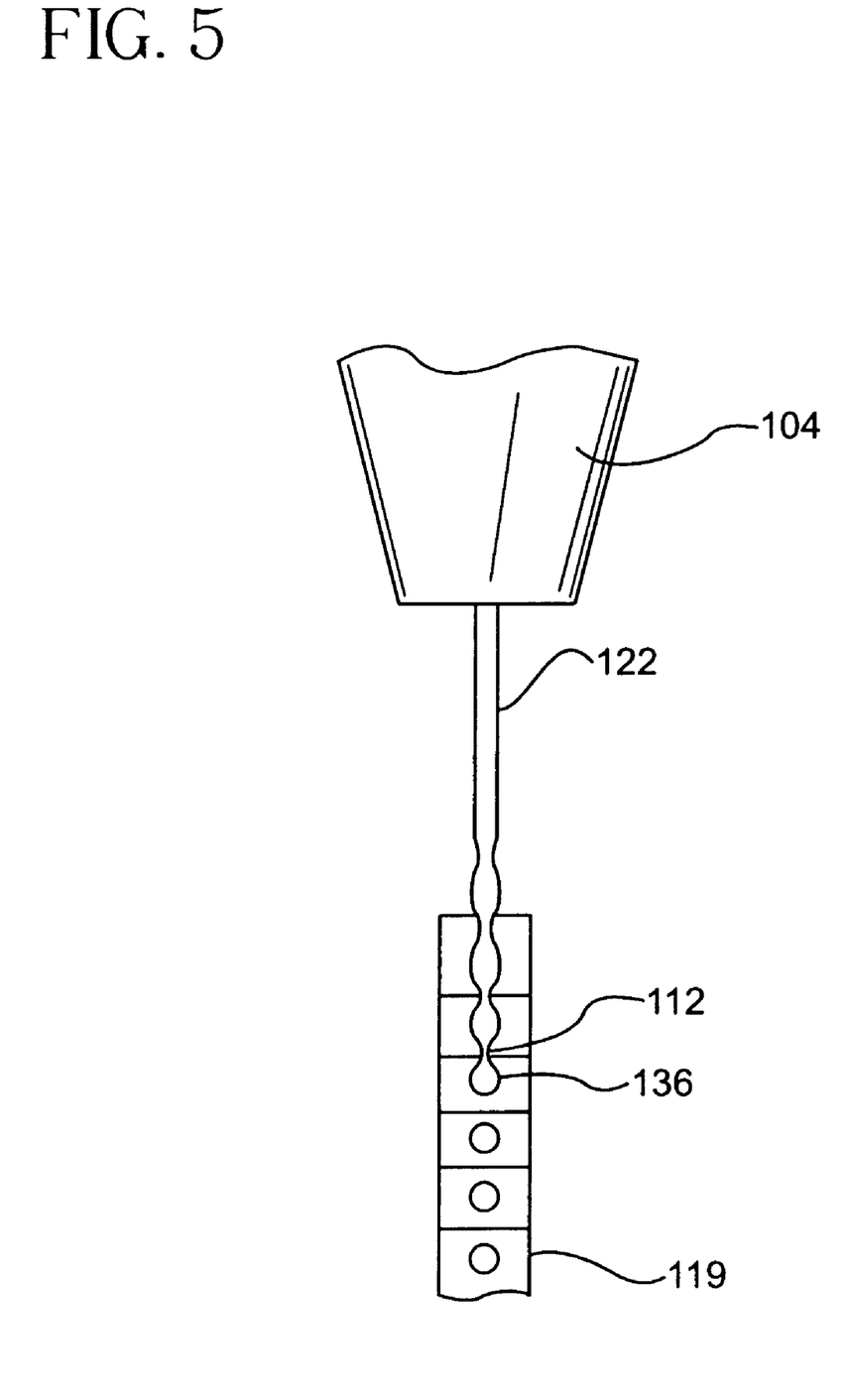
FIG. 5 is a detailed view of the droplet forming area of the flow cytometer shown in FIG. 1.

As shown in FIG. 2, the oscillating device 114 is connected to an alternating voltage source 116 whose output voltage amplitude, frequency and phase is controlled by a controller 118 which can be, for example, a microprocessor or any other suitable controlling device. The amplitude of the alternating voltage signal output by alternating voltage source 116 can be increased or decreased by controller 118 to in turn increase or decrease the distance from opening 110 at which the droplet break-off 112 occurs. Likewise, the frequency of the alternating voltage signal output by alternating voltage source 116 can be increased or decreased by controller 118 to increase or decrease the rate at which droplets of sample fluid are formed at the droplet break-off point 112.

To view the droplet break-off point 112, a light source 119, such as an LED array, can be positioned in the region of the sample fluid stream containing the droplet break-off point 112. The controller 118 can control the light source 119 to strobe at a desired frequency, so that a detector 120, such as a camera or other optical viewing device, can be used to view the region of the sample fluid stream containing the droplet break-off point 112.

Figure 1:
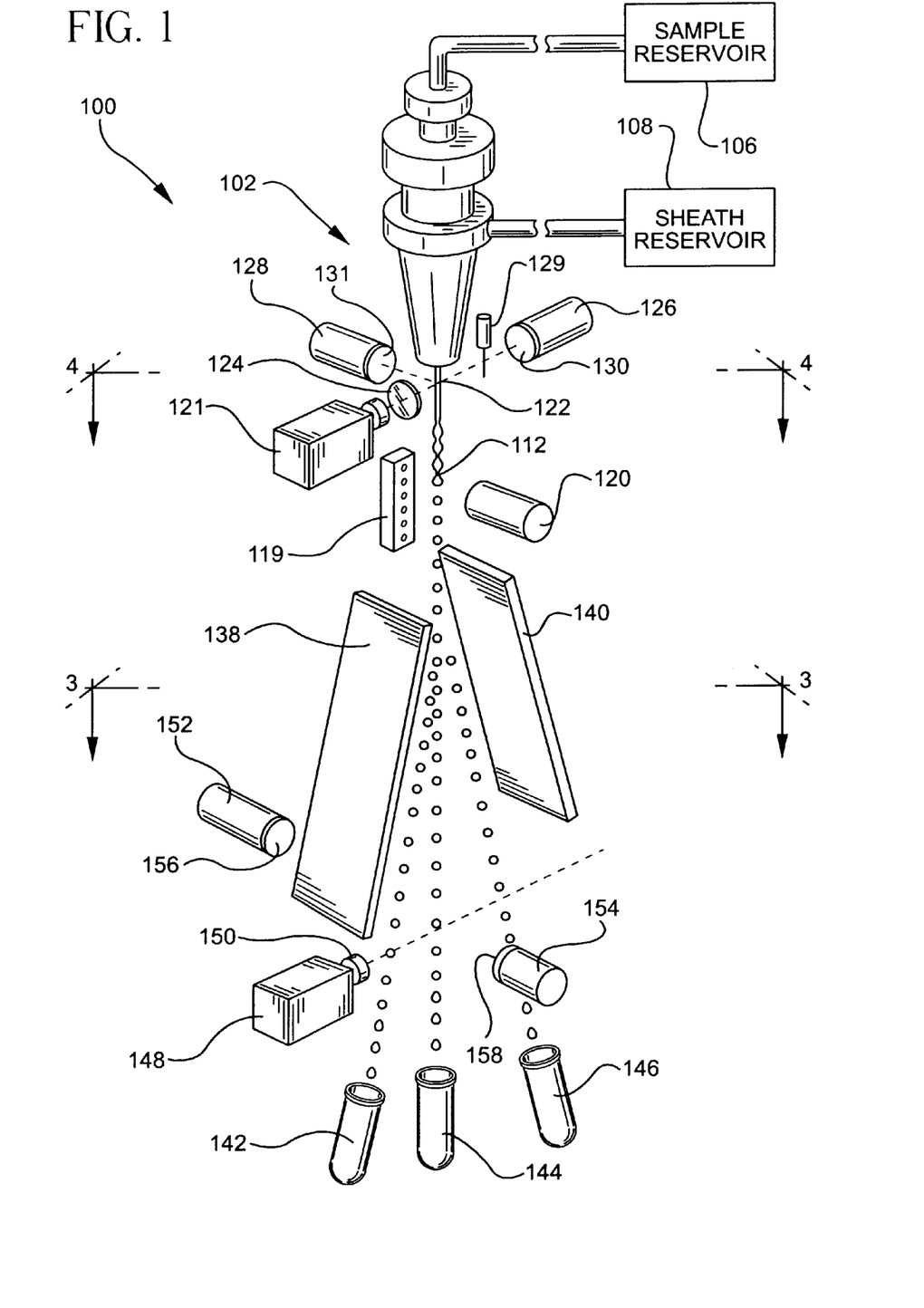
FIG. 1 is a schematic perspective view of a flow cytometer employing an apparatus according to an embodiment of the present invention.

As further discussed in the background section above, the flow cytometer 100 includes a laser 121, such as a diode laser, which is controlled by controller 118 to emit laser light. The emitted laser light intersects the sample stream at a point of interest 122 commonly referred to as the interrogation point. Also, if desired, a lens or filter 124 can be positioned between the laser 121 and the interrogation point 122 to filter out light of unwanted wavelengths from the laser light prior to its reaching the interrogation point 122.

The flow cytometer 100 further includes detectors 126 and 128 which can be, for example, photomultiplier tubes (PMTs), or any other suitable type of light detecting device. As discussed in the background section above, when the laser light intersects the sample stream at the interrogation point 122, the laser light is scattered by the sample stream fluid and, in particular, by any cells present in the sample stream. A portion of the scattered laser light will propagate in a direction substantially consistent with the direction of propagation prior to intersecting the sample stream, and is commonly referred to as the forward scatter laser light. Additionally, a portion of the laser light intersecting the interrogation point 122 will be scattered at an angle with respect to its direction of propagation, and is commonly referred to as side scatter laser light.

As shown in FIGS. 1 and 2, the detectors 126 and 128 are positioned to detect the forward scatter laser light and side scatter laser light, respectively. The detectors 126 and 128 can also detect fluorescent light emitted from the sample stream and, in particular, any cells in the sample stream which pass through the interrogation point. Although detectors 126 and 128 are shown as individual detectors for exemplary purposes, a plurality of detectors can be used to detect the forward and side scatter laser light, as well as to detect fluorescent light. Also, if desired, an obscuration bar 129 can be positioned in the path of the forward scatter laser light, in the path of the side scatter laser light, or both, to reduce the amount of forward scatter laser light, side scatter laser light, or both, detected by detectors 126 and 128, respectively. Furthermore, filters 130 and 131 can be positioned in front of the light receiving areas of detectors 126 and 128, respectively, to filter out any light at wavelengths other than that of the forward scatter laser light and side scatter laser light, respectively.

Laser 121, as well as detectors 126 and 128, are each connected to and controlled by controller 118. Specifically, controller 118 can control the times at which laser 121 emits light toward the interrogation point 122, and can control the times during which detectors 126 and 128 detect the forward scatter laser light and side scatter laser light, respectively. Detectors 126 and 128 each convert the light they receive into electrical signals which are interpreted by controller 118 as representing a characteristic of the sample fluid at the interrogation point 122 at a give sampling time.

That is, the controller 118 analyzes the signals received from detectors 126 and 128 representing characteristics of the sample fluid at an instant in time to determine, for example, whether a particle of interest, such as a cell or fluorescent bead, was present in the sample fluid at the interrogation point 122 at that particular instant in time. The controller 118 can also determine the characteristics of the detected cell based on the characteristics of the signals received from detectors 126 and 128. In particular, the controller 118 can determine the size of the cell based on characteristics of the detected forward scatter laser light, and can determine the cell complexity and granularity based on characteristics of the detected side scatter laser light. As discussed in more detail below, the controller 118 can then take further action depending on the results of the detection.

In particular, the controller 118 can control a charging unit 132 to charge the sample fluid stream at the appropriate time when a cell of interest which was detected at the interrogation point 122 is present in a droplet breaking off from the sample fluid stream, so that the cell can be sorted. That is, as discussed above, the oscillation of oscillation device 114 causes the sample fluid stream to break-off into individual droplets 136 at the droplet break-off point 112. The charging unit 132 includes an output electrode 134 that contacts the mixture of sample fluid and sheath fluid in flow cell 104.

At the appropriate time when the cell detected at the interrogation point 122 is presumed to be present in the droplet 136 forming at droplet break-off point 112, the controller 118 controls the charging unit 132 to charge the sample fluid stream at a desired polarity. This charge is therefore transferred to the droplet 136 presumably containing the cell of interest. The charged droplet 136 then passes between deflection plates 138 and 140, to which are applied opposite polarity DC potentials, such as +2,500 V and −2,500 V, respectively. Depending on the polarity of charge applied to droplet 136, the droplet 136 will either be attracted to deflection plate 138 and repelled by deflection plate 140, or vice-versa. That is, if a positive charge has been applied to droplet 136, droplet 136 will be attracted to deflection plate 140 to which a negative potential is being applied, and will be repelled by deflection plate 138 to which a positive potential is being applied. Conversely, if a negative charge has been applied to droplet 136, droplet 136 will be attracted to deflection plate 138 and repelled by deflection plate 140.

As further illustrated, the flow cytometer includes a plurality of collection vessels 142, 144 and 146. Droplets that have been negatively charged will be directed by the potentials applied to the deflection plates 138 and 140 toward collection vessel 142. Droplets 136 which have been neither positively nor negatively charged will not be deflected by the potentials applied to deflection plates 138 and 140, and therefore continue along their original path into central collection vessel 144. Droplets 136 which have been positively charged will be deflected by the potentials applied to deflection plates 138 and 140 toward collection vessel 146.

As can be appreciated from the above, in order for the controller 118 to control the charging unit 132 to charge the appropriate droplets 136 containing detected cells of interest, it is critical that the drop delay that exists between the time at which a cell of interest is detected at the interrogation point to the time at which the charge is applied to the droplet presumably containing that cell be accurately determined. Ideally, the drop delay should substantially correspond to the time that elapses during which a cell of interest travels from the interrogation point 122 to a location that substantially corresponds to the droplet break-off point 112 to insure that the cell of interest is in the droplet being charged. However, known techniques for estimating the drop delay suffer from the drawbacks discussed in the background section above.

Therefore, in accordance with an embodiment of the present invention, a droplet analyzing apparatus is positioned to analyze the content of droplets 136 that have passed through the deflection plates 138 and 140, to determine whether the droplets 136 presumably containing cells of interest detected at the interrogation point 122 are being properly charged. In other words, the analyzing apparatus empirically verifies the results of the sorting "on the fly" as the sorting is being performed, to thereby verify whether the drop delay has been properly set.

The droplet analyzing apparatus includes a second light source 148, such as a laser diode or any other suitable light emitting source that emits light of an appropriate wavelength which can, for example, be a wavelength that will excite fluorescent materials present in the droplets 136, or that will be scattered by cells in the droplets 136. The light source 148 is positioned to emit light in a direction which intersects the paths of the droplet streams as deflected by the potentials applied to deflection plates 138 and 140, so that the presence or absence of cells of interest in those droplet streams can be detected. Light source 148 can be controlled by controller 118 to emit light in a continuous or pulsed manner. A filter 150 can be positioned between the light source 148 and the droplet streams to filter out any light at undesired wavelengths from the light emitted by the light source 148 before it reaches the droplet streams.

The droplet analyzing apparatus further includes a detector 152, such as a PMT or any other suitable type of light detector. The droplet analyzing apparatus can further include a second detector 154, such as a video camera or any other type of optical viewing device, which can be used to view the droplet streams as they intersect the light beam emitted by light source 148. Although detectors 152 and 154 are represented as single detectors for exemplary purposes, multiple detectors can be used. Also, filters 156 and 158 can be positioned between the detectors 152 and 154, respectively, and the droplet streams to prevent light at undesired wavelengths from entering detectors 152 and 154.

Detector 152 is connected to and thus controlled by controller 118 to detect light either continuously or at the appropriate intervals with respect to the emission of light by the light source 148. Detector 152 converts the detected light signals to provide an indication to controller 118 as to the presence or absence of cells of interest in the droplet streams.

An example of the manner in which light source 148 and detectors 152 and 154 are used to monitor and adjust the drop delay will now be described. When the flow cytometer 100 is being calibrated prior to sorting an actual cell sample, beads having fluorescent and physical characteristics of cells of interest are added to sample reservoir 106. Suitable beads are 6 µm far red beads manufactured by Molecular Probes, Inc., 6 µm yellow/green beads manufactured by Polysciences, or any other beads having a size and characteristics similar to those of the types of cells to be analyzed. The flow cytometer 100 delivers the beads in sample reservoir 106 along with the sheath fluid in sheath reservoir 108 to flow cell 104 of the nozzle 102 in the manner described above. The beads and sheath fluid combine in the flow cell 104, and exit the flow cell 104 through opening 110 as a sample fluid stream.

The controller 118 controls the laser 121 and detectors 126 and 128 to detect the presence of a sample bead at the interrogation point 122 in the sample fluid stream. The controller 118 can determine whether a sample bead is present at the interrogation point 122 based on, for example, characteristics of the forward scatter laser light, side scatter light, or both, as detected by detectors 126 and 128; based on the fluorescent light detected by either or both of detectors 126 and 128; or based on a combination of detected forward scatter laser light, side scatter laser light, and fluorescence.

When the controller 118 determines that a sample bead is present at interrogation point 122, the controller 118 controls the charging unit 132 to charge the sample fluid stream after a predetermined period of time has elapsed (i.e., the drop delay time). This drop delay time is set to correspond to the estimated drop delay time during which the detected bead travels from the interrogation point 122 to the droplet break-off point. The drop delay is set in this manner so that the controller 118 will charge a droplet that is formed at the time when the detected sample bead is presumed to be present at the droplet break-off point 112.

The charged droplet is then deflected as appropriate by the potentials applied to deflection plate 138 and 140. This charging and sorting process is performed each time a bead is detected at the interrogation point 122. Accordingly, as the process continues, if the drop delay time set by the controller 118 is correct, the detected sample beads will indeed be present at the droplet break-off point 112 at the time droplets are charged. Therefore, the droplets containing the sample beads will be charged, and thus deflected in the appropriate manner by deflection plates 138 and 140. In this example, it is assumed that the droplets 136 are being charged with a negative potential each time a bead is detected, and are therefore deflected by deflection plates 138 and 140 into the droplet stream being collected in collection vessel 142 (hereinafter, the "left droplet stream").

Assuming that the light being emitted by light source 148 is of a wavelength which excites the sample beads, when the sorted and unsorted droplets 136 pass through the light emitted by light source 148, the light excites the sample beads contained in the droplets 136 and causes them to emit fluorescent light of a particular wavelength. Filters 156 and 158 permit the fluorescent light to pass to their respective detectors 152 and 154, while blocking light of undesired wavelengths. Detector 152 provide signals to the controller 118 representing the detected fluorescence. Alternatively, as discussed above, detector 152 can detect the light being scattered by the beads, and provide signals to the controller 118 representing the detected scattered light.

If the droplets believed to contain detected beads are being charged at the appropriate drop delay time, then the droplets in the left droplet stream should contain the sample beads. Accordingly, the detectors 152 and 154 should detect the absence of fluorescence (or scattered light) at this wavelength in central droplet stream being collected in collection vessel 144, as well as in the droplet stream being collected in collection vessel 146 (hereinafter, the "right droplet stream"), while also detecting the presence of fluorescence (or scattered light) at this wavelength in the left droplet stream. However, if the drop delay time set by controller 118 is not causing the charging unit 132 to charge the droplets correctly, droplets other than those containing sample beads will be charged and deflected toward collection vessel 142, while droplets containing sample bead will pass to collection vessel 144. In this event, detectors 152 and 154 will detect an increased presence of fluorescence (or scattered light) at this wavelength in the central droplet stream, while detecting less fluorescence (or scattered light) at this wavelength in the left droplet stream.

The drop delay time can then be adjusted manually or automatically so that droplets actually containing the detected sample beads will be charged and thus deflected toward the appropriate collection vessel. For example, an operator viewing the results detected by detector 154 can manually adjust controller 118 to alter the drop delay time at which charging unit 132 charges the droplet stream, until the operator observes a maximum or otherwise acceptable level of fluorescence (or scattered light) in the left droplet stream and an acceptable minimum level of fluorescence (or scattered light) in the central droplet stream. The controller 118 can also include circuitry which automatically adjusts the drop delay at which the charging unit 132 charges the droplet stream until the signals provided by detector 152 indicate that a maximum or otherwise acceptable level of fluorescence (or scattered light) is present in the left droplet stream, and an acceptable minimum level of fluorescence (or scattered light) is present in the central droplet stream.

Alternatively or in addition, the controller 118 can include circuitry which adjusts parameters such as the pressure of the sheath fluid, sample fluid, or both, as well as the amplitude, frequency and phase of the voltage output by the alternating voltage source 116. The change in pressure of either or both of the sheath and sample fluids changes the distance between the droplet break-off point and interrogation point. The change in parameters such as amplitude, frequency and phase changes the oscillation characteristics of the oscillating device 114, which changes the distance between the droplet break-off point and interrogation point. Also, the operator can manually control the controller 118 to change any of the above parameters. Accordingly, the distance between the interrogation point 122 and droplet break-off point 112 can be made smaller or greater, as necessary, to result in an increased or decreased travel time for the cell between these points, so that the travel time substantially corresponds to the set charging time (i.e., the drop delay time).

Once the appropriate drop delay time has been determined, the sample beads can be removed from sample reservoir 106. An actual fluid sample containing cells to be analyzed and sorted is then added to sample reservoir 106, and the flow cytometer 100 is operated at the droplet charging timing determined during the calibration process.

It is noted that sample beads can also be added to a fluid sample containing cells to be analyzed and sorted to verify the accuracy of the sorting process. In this regard, sample beads having characteristics corresponding to different types of cells of interest that are to be segregated into the left and right droplet streams can be analyzed and sorted along with the sample cells to verify the accuracy of the sorting.

Furthermore, by positioning the droplet analyzing apparatus to detect the left, center and right streams as discussed above, the droplet analyzing apparatus can also be used to verify the positions of those streams. That is, if it is desired to reposition the left stream to better align with collection vessel 142, the controller 118 can control the charging unit 132 to increase the magnitude of the negative potential being applied to the negatively charged droplets. Accordingly, the increased attracting and repelling forces applied to the negatively charged droplets 136 will cause them to be deflected further to the left, thus moving the left droplet stream further left. This effect can also be achieved by the controller increasing and decreasing the potentials applied to the deflection plates 138 and 140 as appropriate. The detector 152 detects this view position of the left droplet stream. The controller 118 can interpret the signals received from detector 152 to verify if the position is correct, and make any further adjustments if necessary.

In addition, the droplet analyzing apparatus need not be positioned to detect the presence or absence of cells of interest in droplets that have already been deflected. Rather, in an embodiment of the present invention shown in FIGS. 6 and 7, the droplet analyzing apparatus is positioned to detect the presence or absence of cells of interest in droplets as the droplets are being formed. In this embodiment, all components identified with numbers corresponding to the components of the embodiment shown in the FIGS. 1–5 are essentially identical to those components.

Figure 6:
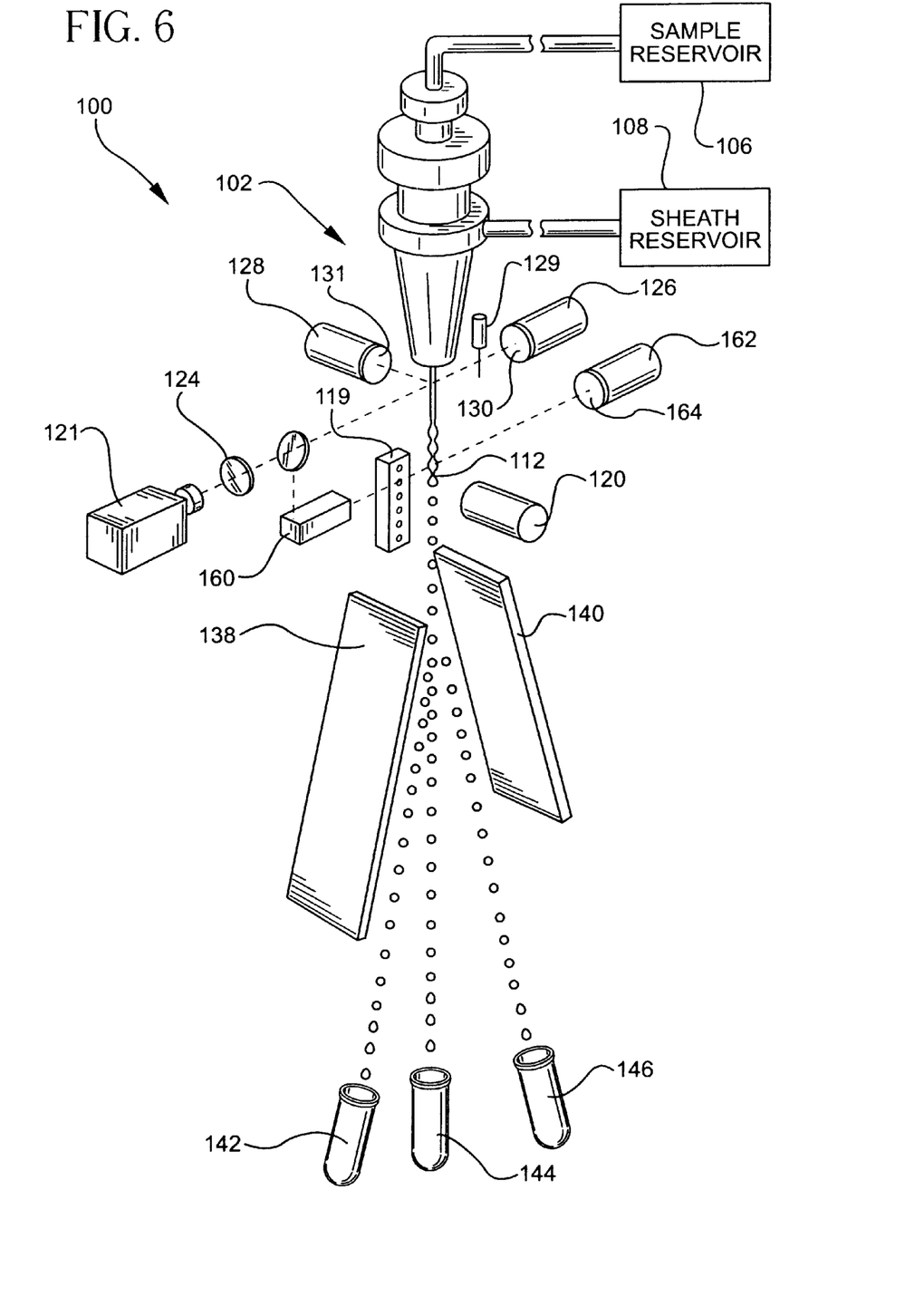
FIG. 6 is a schematic perspective view of a flow cytometer employing an apparatus according to another embodiment of the present invention.
Figure 7:
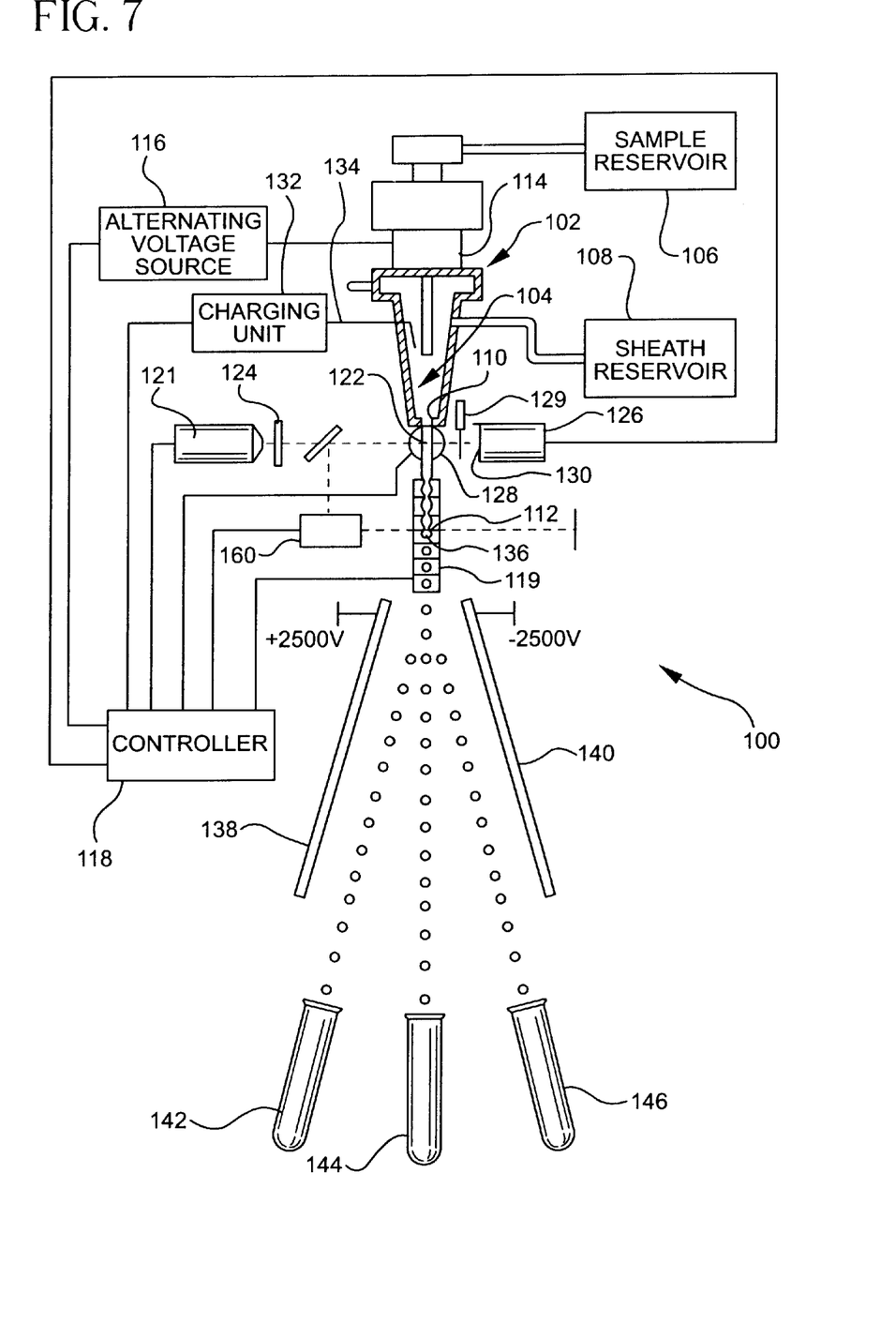
FIG. 7 is a schematic illustration of a front view of a portion of the flow cytometer employing the embodiment shown in FIG. 6.

However, as illustrated, the embodiment shown in FIGS. 6 and 7 includes a light beam splitter which directs a portion of the light output by light source 120 into an acousto-optic modulator 160. A separate light source can instead be used. The controller 118 controls the acousto-optic modulator 160 to emit a pulse of light toward the droplets being formed at the droplet break-off point 112 only when the droplet being formed is being charged. Specifically, the length of the pulse period is a fraction of the duration of time during which the charging pulse is being applied to the droplet.

A detector 162, which can be similar to detector 152, is positioned to detect light being emitted from the droplet and, in particular, fluorescent light at a wavelength corresponding to that emitted by a sample bead, or scattered light scattered by a sample bead. The detector 162 can be coupled to and controlled by controller 118 to detect light only at designated periods of time. Also, like detector 152, detector 162 converts the detected light into electrical signals which are provided to and analyzed by the controller 118. A filter 164 can be positioned in front of detector 164 to block any light at undesired wavelengths from being detected by detector 162.

If the droplet 136 being charged does indeed include a sample bead that was detected at the interrogation point 122, the light emitted from the acousto-optic modulator 160 will excite the bead and cause it to fluoresce, or will be scattered by the bead. The detector 162 will detect the fluorescence (or scattered light), and provide an electrical signal to the controller 118 indicating that a bead is present in the droplet. In this event, the controller circuitry 118 will determine that the drop delay time is correct.

However, if the droplet 136 being charged does not include a sample bead, no fluorescence will be emitted (or the appropriate scattered light will not be detected). The signals provided to the controller 118 by detector 162 will indicate that no bead was present in the droplet being charged. Accordingly, the controller circuitry can continue to adjust the drop delay at which the charging unit 132 charges the droplet in response to detection of a bead at the interrogation point 122, until the detector 162 detects the presence of beads in the droplets being charged.

In addition, the controller can be configured to determine based on the signals from detector 162 whether a bead is present before charging the droplet 136. In this event, if a bead is present in the droplet being analyzed, the desired charging potential is applied. If no bead is present, no charging is applied, and the controller 118 adjusts the drop delay accordingly.

Instead of automatically adjusting the droplet charging timing, an observer can view the droplets being formed to determine whether fluorescence (or scattered light) is present. If little or no fluorescence (or scattered light) is present in the droplets being formed, the observer can manually control the controller 118 to adjust the drop delay at which the charging unit 132 charges the droplets until an acceptable level of fluorescence (or scattered light) is detected from the droplets being formed, thus indicating that droplets containing beads are being properly charged and sorted. The controller 118 could also automatically or manually adjust the fluid pressures, as well as the parameters of the voltage being applied to the oscillating device 114 by the alternating voltage source 114, to adjust the distance between the droplet break-off point 112 and the interrogation point 122.

Figure 8:
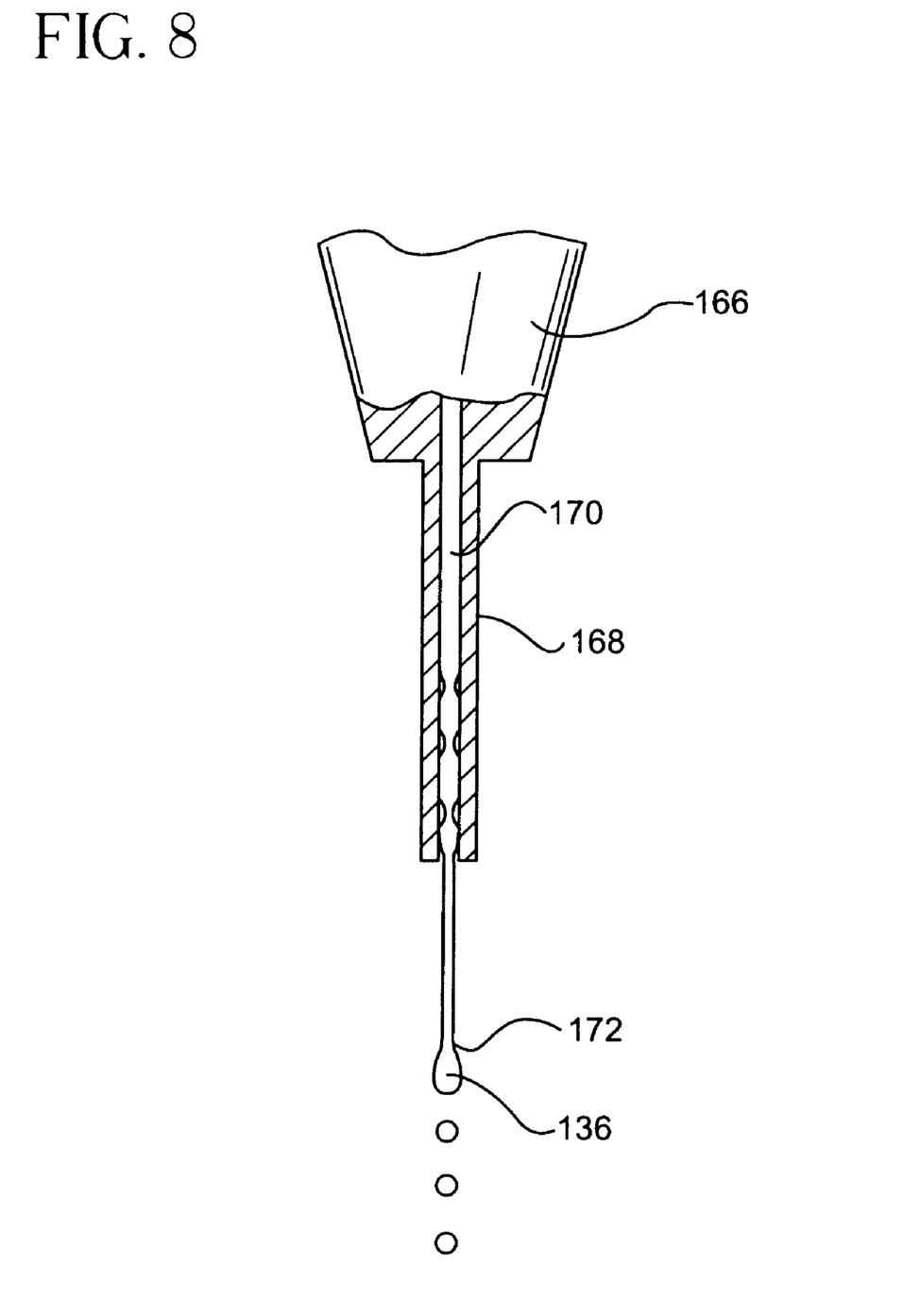
FIG. 8 is a schematic illustration of an alternate configuration of a nozzle of a flow cytometer employing the embodiments shown in FIGS. 1 and 6.

The embodiments described above can be used effectively with any type of flow cytometer nozzle. In particular, the above embodiments can be used effectively with a cuvette nozzle configuration as shown in FIG. 8. Nozzle 166 is similar to nozzle 102 described above. However, nozzle 166 includes a cuvette 168 made of a substantially clear material such as clear plastic or any other suitable material. In this configuration, the interrogation point 170 is present in the cuvette 168, while the droplet break-off point 172 is present at a distance from the opening in the cuvette 168 from which the sample stream exits.

Due to the dimensions and overall construction of the cuvette 168, the flow rate of the sample fluid in the cuvette 168 is much slower than the flow rate of the sample fluid once it exits the cuvette 168 (e.g., 6 m/sec versus 28 m/sec). This slower flow rate in the cuvette 168 causes the cells of interest to pass through the interrogation point 170 at a slower rate, which allows their characteristics to be measured more precisely. Moreover, because the characteristics on which the analyses performed by the embodiments described above are not dependent on the flow rate of the sample fluid, the accuracy of the analysis is not adversely affected by the different flow rates of the sample fluid experienced in and out of the cuvette 168.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An apparatus, for use in a flow cytometer, for verifying accuracy of a drop delay setting representing a period of time elapsing between a moment at which any of a plurality of particles in a fluid flowing through said flow cytometer is detected at a reference location and a moment at which a sorting condition is applied in response to said detection of a droplet of said fluid forming at a droplet forming location, said apparatus comprising:
    a first detector, adapted to detect a presence of at least one of said particles at said reference location; and
    a second detector, adapted to detect a presence or absence of said at least one of said particles within at least one intact droplet either at formation or in freefall at a droplet detection location downstream of said reference location to provide an indication of the accuracy of said drop delay.

2. An apparatus as claimed in claim 1, wherein:
    said droplet detection location is at a distance downstream of said droplet forming location.

3. An apparatus as claimed in claim 1, wherein:
    said droplet detection location is downstream of a location in said flow cytometer in which said droplets are sorted.

4. An apparatus as claimed in claim 1, further comprising:
    a controller which controls applying said sorting condition to said droplet at said droplet forming location based on said presence or absence of said at least one of said particles within said droplet detected by said second detector, said sorting condition including applying a charging potential to said droplet.

5. An apparatus as claimed in claim 4, wherein:
    said controller automatically controls applying said charge to said droplet at said droplet forming location.

6. An apparatus as claimed in claim 1, wherein:
    said second detector detects a presence or absence of said at least one of said particles within each of a plurality of droplets at said droplet detection location.

7. An apparatus as claimed in claim 1, wherein said second detector is adapted to the detect a presence or absence of said at least one of said particles within at least one intact droplet while said droplet is in freefall.

8. An apparatus as claimed in claim 1, wherein said second detector is adapted to detect the presence of said at least one of said particles within at least one intact droplet.

9. An apparatus as claimed in claim 1, wherein said second detector is adapted to detect the absence of said at least one of said particles within at least one intact droplet.

10. An apparatus, for use in a flow cytometer, for verifying accuracy of a drop delay setting representing a period of time elapsing between a moment at which any of a plurality of particles in a fluid flowing through said flow cytometer is detected at a reference location and a moment at which a sorting condition is applied in response to said detection of a droplet of said fluid forming at a droplet forming location, said apparatus comprising:

a first detector, adapted to detect a presence of at least one of said particles at said reference location; and a second detector, adapted to detect a presence or absence of said at least one of said particles within at least one intact droplet at a droplet detection location downstream of said reference location to provide an indication of the accuracy of said drop delay;

wherein said droplet detection location substantially corresponds to said droplet forming location.

11. A method for verifying accuracy of a drop delay setting in a flow cytometer, said drop delay representing a period of time elapsing between a moment at which any of a plurality of particles in a fluid flowing through said flow cytometer is detected at a reference location to a moment at which a sorting condition is applied in response to said detection of a droplet of said fluid forming at a droplet forming location, said method comprising the steps of:

detecting a presence of at least one of said particles at said reference location; and detecting a presence or absence of said at least one of said particles within at least one intact droplet during formation or in freefall at a droplet detection location downstream of said reference location to provide an indication of the accuracy of said drop delay.

12. A method as claimed in claim 11, wherein:

said droplet detection location is at a distance downstream of said droplet forming location.

13. A method as claimed in claim 11, wherein:

said droplet detection location is downstream of a location in said flow cytometer in which said droplets are sorted.

14. A method as claimed in claim 13, wherein:

said droplet presence or absence detection step detects said presence or absence of said at least one of said particles within said droplet which has been sorted by said flow cytometer.

15. A method as claimed in claim 11, wherein:

said droplet presence or absence detection step detects said presence or absence of said at least one of said particles within said droplet which is an unsorted droplet.

16. A method as claimed in claim 11, further comprising the step of:

controlling application of said sorting condition to said droplet at said droplet forming location based on said detected presence or absence of said at least one of said particles within said intact droplet, said sorting condition including applying a charging potential to said droplet.

17. A method as claimed in claim 16, wherein:

said controlling step automatically controls said charging of said droplet at said droplet forming location.

18. A method is claimed in claim 11, wherein:

said presence or absence detecting step detects a content of each of a plurality of droplets at said droplet detection location.

19. A method as claimed in claim 11, wherein said step of detecting the presence or absence of said at least one of said particles within said at least one intact droplet occurs while said droplet is in freefall.

20. A method as claimed in claim 11, wherein said step of detecting the presence or absence of said at least one of said particles within said at least one intact droplet detects the presence of said particles.

21. A method as claimed in claim 11, wherein said step of detecting the presence or absence of said at least one of said particles within said at least one intact droplet detects the absence of said particles.

22. A method for verifying accuracy of a drop delay setting in a flow cytometer, said drop delay representing a period of time elapsing between a moment at which any of a plurality of particles in a fluid flowing through said flow cytometer is detected at a reference location to a moment at which a sorting condition is applied in response to said detection of a droplet of said fluid forming at a droplet forming location, said method comprising the steps of:

detecting a presence of at least one of said particles at said reference location; and detecting a presence or absence of said at least one of said particles within at least one intact droplet at a droplet detection location downstream of said reference location to provide an indication of the accuracy of said drop delay wherein said droplet detection location substantially corresponds to said droplet forming location.

* * * * *